United States Patent
Kessel et al.

(10) Patent No.: US 6,759,553 B1
(45) Date of Patent: Jul. 6, 2004

(54) PROCESS FOR THE PREPARATION OF CREATINE OR CREATINE MONOHYDRATE

(75) Inventors: Knut Kessel, Mannheim (DE); Günter Scherr, Ludwigshafen (DE); Michael Kluge, Ludwigshafen (DE); Norbert Biedermann, Bad Dürkheim (DE); Thomas Greindl, Bad Dürkheim (DE); Thomas Bogenstätter, Bad Dürkheim (DE); Wolfgang Hähnlein, Freinsheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 285 days.

(21) Appl. No.: 09/391,384

(22) Filed: Sep. 8, 1999

(51) Int. Cl.⁷ .............................................. C07C 249/02
(52) U.S. Cl. ...................................................... 562/560
(58) Field of Search ......................................... 562/560

(56) References Cited

U.S. PATENT DOCUMENTS 2,574,510 A   11/1951   Thurston et al. ............. 260/501
2,654,779 A   10/1953   Vassel et al. ................. 260/534
5,719,319 A    2/1998   Weiss et al. .................. 562/560

FOREIGN PATENT DOCUMENTS

EP   754679   1/1997
JP   077364   6/1978

OTHER PUBLICATIONS

Database CAPLUS on STN, Acc. No. 1992:455232, Takahashi et al., 'Apparatus for treating wastewaters with controlled pH adjustment.' JP 04040288 A2 (abstract), 1992.*
Ullmann's Enc. of Ind. Chem., 5th Ed., vol. A12, pp. 552–553, 1987.

* cited by examiner

Primary Examiner—Johann Richter
Assistant Examiner—Brian J. Davis
(74) Attorney, Agent, or Firm—Keil & Weinkauf

(57) ABSTRACT

A process for the preparation of creatine or creatine monohydrate by reaction of sodium or potassium sarcosinate with cyanamide at a temperature from 20 to 150° C. and a pH from 7.0 to 14.0 comprises carrying out the pH adjustment with carbonic acid.

7 Claims, No Drawings

PROCESS FOR THE PREPARATION OF CREATINE OR CREATINE MONOHYDRATE

BACKGROUND OF THE INVENTION

The present invention relates to a process for the preparation of creatine or creatine monohydrate by reaction of sodium or potassium sarcosinate with cyanamide.

Creatine [N-amidinosarcosine] is a natural substance occurring mainly in the muscle tissue of the vertebrates. As creatine phosphate, it forms an important energy reserve of the muscle. For this reason, creatine is particularly used by athletes as a food supplement.

The industrial processes for the preparation of creatine are carried out by reaction of sarcosine or sodium or potassium sarcosinate with cyanamide or O-methylisourea and are described, inter alia, in Ullmann's Encyclopedia of Industrial Chemistry, 5th Edition, Volume A 12, 552, VCH-Verlagsgesellschaft, Weinheim (1987), and in the following patent specifications: U.S. Pat. No. 2,654,779, EP-A-0 754 679 and JA 53-077364 and the continuing literature cited there.

According to the abovementioned prior art, the reaction takes place under basic conditions, advantageously at a pH of between 9 and 10. In the reaction of aqueous, technical sodium or potassium sarcosinate solution which has a pH of greater than 10, the adjustment of the pH is carried out by addition of inorganic or organic acids, in particular by addition of aqueous hydrochloric or sulfuric acid and by means of acetic acid or formic acid.

The strongly corrosive properties of hydrochloric acid make the use of expensive materials, for example enamel reactors or special glass equipment, necessary. The pH regulation by means of sulfuric acid can lead to the precipitation of sodium sulfate and thus to an adverse effect on the product purity of creatine. The use of organic acids such as formic acid and acetic acid leads to increased waste water pollution by organic carbon, whose content in the waste water of large-scale industrial processes should be kept as low as possible for ecological reasons. Moreover, the pH adjustment with the abovementioned acids necessitates a considerable outlay on measurement and regulation technology.

THE INVENTION

It is therefore an object of the present invention to make available an inexpensive and simple to carry out process for the preparation of creatine or creatine monohydrate, which does not have the disadvantages outlined above.

We have found that this object is achieved by a process for the preparation of creatine or creatine monohydrate by reaction of sodium or potassium sarcosinate with cyanamide at a temperature from 20 to 150° C. and a pH from 7.0 to 14.0, which comprises carrying out the pH adjustment with carbonic acid.

Surprisingly, it has been shown that, for the adjustment of the pH of 7.0 to 14.0, a single addition of carbonic acid to the aqueous sodium or potassium sarcosinate solution suffices. Owing to the buffer action of the system sarcosinate/$H_2CO_3$, no further addition of carbonic acid for pH regulation is necessary even during the subsequent reaction with cyanamide. Thus an expensive, pH-controlled metering device can be dispensed with, whereby the entire process for the preparation of creatine is significantly simplified.

The carbonic acid used for the pH adjustment can be prepared by introduction of gaseous carbon dioxide or by addition of solid carbon dioxide, so-called dry ice. The use of gaseous carbon dioxide is preferred for the preparation of the carbonic acid used according to the invention.

The pH during the reaction of sodium or potassium sarcosinate with cyanamide lies in the alkaline range between 7.0 and 14.0, preferably between 8.0 and 12.0, particularly preferably between 9.0 and 10.0.

The reaction temperature lies in the range from 20 to 150° C., preferably from 30 to 120° C., particularly preferably in the range from 50 to 100° C., the reaction optionally being carried out under pressure.

The aqueous sodium or potassium sarcosinate solution is a 5 to 60% strength by weight, preferably 35 to 45% strength by weight, aqueous solution.

Cyanamide is preferably employed in the form of a 50% strength by weight aqueous solution.

The molar ratio cyanamide to sodium or potassium sarcosinate can be varied within wide limits. Preferably, this ratio lies in the range between 1:3 and 3:1, particularly preferably between 1:1 and 1:1.5.

The reaction according to the invention of sodium or potassium sarcosinate with cyanamide can be carried out both batchwise and continuously.

PREFERRED EMBODIMENTS

In a preferred embodiment, an aqueous, technical sodium or potassium sarcosinate solution is adjusted with carbonic acid to a pH of between 7.0 and 14.0, preferably between 8.0 and 12.0, particularly preferably between 9.0 and 10.0. The carbonic acid used for this purpose is prepared by introducing $CO_2$ into the aqueous sarcosinate solution at temperatures between 10 and 50° C., preferably between 20 and 40° C. The solution adjusted to the desired pH is then treated with cyanamide, in particular with a 40 to 60% strength by weight aqueous cyanamide solution, over a period of time of 0.5 to 8 hours, preferably 1 to 5 hours. The temperature during the addition lies in the range from 20 to 150° C., preferably from 30 to 120° C., particularly preferably in the range from 50 to 100° C. During the addition of cyanamide, a further pH regulation by carbonic acid can be dispensed with in this reaction sequence. After the addition of cyanamide, it is advantageous to stir the reaction mixture until reaction of the cyanamide at the abovementioned temperature is complete.

It is also possible to carry out the reaction in an aqueous-organic solvent system, for example in an aqueous-alcoholic system in the presence of an alcohol, such as, for example, methanol, ethanol or isopropanol.

The isolation of creatine or creatine monohydrate is carried out in a manner known per se. Thus, for example, the product of value can be obtained in crystalline form by cooling the reaction solution to −20 to 60° C., in particular 0 to 40° C. After filtration, the purity can optionally be improved by a further recrystallization. However, it is also possible to remove the product from the reaction mixture by means of extraction in order to subsequently isolate it in clean form by distillation or crystallization.

In the following example, the process for the preparation of creatine is explained in greater detail.

EXAMPLE

Preparation of Creatine 1315 g of a 40% strength aqueous sodium sarcosinate solution (pH 14) were introduced into a 2 l three-necked flask having a mechanical stirrer, heating bath, reflux condenser and gas inlet tube and the mixture was adjusted to pH 9 by introduction of carbon dioxide gas. After heating the solution to 75° C., 338 g of a 50% strength aqueous cyanamide solution were added in the course of 4 hours. The temperature was kept constant at 75° C. during the entire addition period. The pH remained between 9 and 10 without introduction of further $CO_2$ gas. After the addition of cyanamide, the reaction solution was stirred for 2 hours and then cooled to 35° C. The precipitated creatine was filtered off, washed with water and dried. 480 g of creatine monohydrate having a crystal yield of 75% were obtained.

We claim:

1. In a process for the preparation of creatine or creatine monohydrate by reaction of sodium or potassium sarcosinate with cyanamide at a temperature of from 20 to 150° C. and a pH from 7.0 to 14.0, the improvement which comprises carrying out the pH adjustment with carbonic acid.

2. A process as claimed in claim 1, wherein the carbonic acid used for the pH adjustment is prepared by introduction of $CO_2$ gas or by addition of dry ice.

3. A process as claimed in claim 1 wherein the pH is adjusted to 9.0 to 10.0.

4. A process as claimed in claim 1 wherein the reaction is carried out at a temperature from 50 to 100° C.

5. A process as claimed in claim 1, wherein the sodium or potassium sarcosinate is employed in the form of a 35 to 45% strength by weight aqueous solution.

6. A process as claimed in claim 1 wherein cyanamide is employed in the form of a 40 to 60% strength by weight aqueous solution.

7. A process for the preparation of creatine or creatine monohydrate, which comprises a) adjusting an aqueous sodium or potassium sarcosinate solution to a pH from 7.0 to 14.0 using carbonic acid and b) treating the resulting solution with an aqueous solution of cyanamide at a temperature from 20 to 150° C., with no further addition of carbonic acid.

\* \* \* \* \*